US012637421B2

(12) United States Patent
Ogawa et al.

(10) Patent No.: US 12,637,421 B2
(45) Date of Patent: May 26, 2026

(54) ANTHRAQUINONE COMPOUND, LIQUID CRYSTAL COMPOSITION CONTAINING SAID COMPOUND, AND DIMMING ELEMENT

(71) Applicant: NIPPON KAYAKU KABUSHIKI KAISHA, Tokyo (JP)

(72) Inventors: Kanae Ogawa, Tokyo (JP); Kohei Ohtani, Tokyo (JP); Masakazu Shiraishi, Tokyo (JP); Hitomi Muto, Tokyo (JP); Saori Suzuki, Tokyo (JP)

(73) Assignee: NIPPON KAYAKU KABUSHIKI KAISHA, Tokyo (JP)

( * ) Notice: Subject to any disclaimer, the term of this patent is extended or adjusted under 35 U.S.C. 154(b) by 245 days.

(21) Appl. No.: 18/708,400

(22) PCT Filed: Nov. 29, 2022

(86) PCT No.: PCT/JP2022/043896
§ 371 (c)(1),
(2) Date: Oct. 15, 2024

(87) PCT Pub. No.: WO2023/100848
PCT Pub. Date: Jun. 8, 2023

(65) Prior Publication Data

US 2025/0304531 A1 Oct. 2, 2025

(30) Foreign Application Priority Data

Dec. 1, 2021 (JP) ................................ 2021-195060

(51) Int. Cl.
*C07C 323/38* (2006.01)
*C09K 19/12* (2006.01)
*C09K 19/60* (2006.01)

(52) U.S. Cl.
CPC ............ *C07C 323/38* (2013.01); *C09K 19/12* (2013.01); *C09K 19/603* (2013.01); *C09K 2019/123* (2013.01)

(58) Field of Classification Search
CPC .... C07C 323/38; C09K 19/12; C09K 19/603; C09K 2019/123
See application file for complete search history.

(56) References Cited

U.S. PATENT DOCUMENTS

| | | | |
|---|---|---|---|
| 4,126,626 | A | 11/1978 | Jost |
| 2009/0098314 | A1 | 4/2009 | Takaku et al. |
| 2010/0227084 | A1 | 9/2010 | Kato et al. |
| 2018/0307077 | A1 | 10/2018 | Miura et al. |

FOREIGN PATENT DOCUMENTS

| | | | | |
|---|---|---|---|---|
| EP | 4282934 | A1 * | 11/2023 | ......... C09B 67/0038 |
| EP | 4324823 | A1 * | 2/2024 | ............... C09B 1/58 |
| GB | 2082196 | A | 3/1982 | |

(Continued)

OTHER PUBLICATIONS

International Search Report mailed Feb. 21, 2023 in corresponding PCT application No. PCT/JP2022/043896.

*Primary Examiner* — Bijan Ahvazi

(74) *Attorney, Agent, or Firm* — Nields, Lemack & Frame, LLC

(57) ABSTRACT

The present invention is an anthraquinone compound represented by formula (1) (in the formula, $R_1$ represents a hydrogen atom, a straight chain or branched chain alkyl group having a carbon count of 1-12, or a straight chain or branched chain alkoxy group having a carbon count of 1-12. $R_2$ represents a hydrogen atom, a straight chain or branched chain alkyl group having a carbon count of 1-8, or a straight chain or branched chain alkoxy group having a carbon count of 1-8). $R_2$ may be a straight chain or branched chain alkyl group having a carbon count of 1-8. $R_1$ may be a straight chain or branched chain alkoxy group having a carbon count of 1-8, or may be a straight chain or branched chain alkyl group having a carbon count of 1-4. The present invention also relates to a dimming liquid crystal composition containing this anthraquinone compound and a liquid crystal material. The present invention also relates to a dimming element obtained by sandwiching the dimming liquid crystal composition or a photocured product thereof between a pair of substrates disposed facing each other, at least one among which is a transparent substrate having a transparent electrode.

(1)

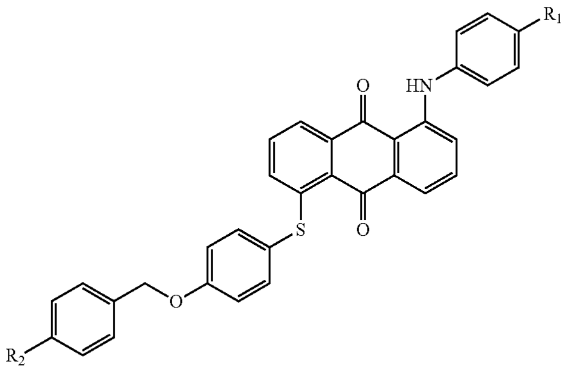

20 Claims, No Drawings

(56) References Cited

FOREIGN PATENT DOCUMENTS

| | | | |
|---|---|---|---|
| JP | 63-72759 | A | 4/1988 |
| JP | 63-72760 | A | 4/1988 |
| JP | 63-501512 | A | 6/1988 |
| JP | 3-47392 | A | 2/1991 |
| JP | 2000-336366 | A | 12/2000 |
| JP | 2009-108295 | A | 5/2009 |
| JP | 2011-190314 | A | 9/2011 |
| JP | 2018-205746 | A | 12/2018 |
| WO | 87/01822 | A1 | 3/1987 |
| WO | 2022/158493 | A1 | 7/2022 |
| WO | 2022/220212 | A1 | 10/2022 |

* cited by examiner

ANTHRAQUINONE COMPOUND, LIQUID CRYSTAL COMPOSITION CONTAINING SAID COMPOUND, AND DIMMING ELEMENT

TECHNICAL FIELD

The present invention relates to a novel anthraquinone compound, a liquid crystal composition containing the compound and a light control element.

BACKGROUND ART

For the purpose of privacy protection, in windows, doors and partitions of vehicles such as trains and automobiles, buildings such as business buildings and hospitals, e.g., films obtained by dispersing a liquid crystal in a polymer and films in which a light control layer is formed by utilizing the property that a liquid crystal substance undergoes phase separation during photocuring of a composition containing a photocurable compound and liquid crystal have been commonly used as light control panels in place of blinds. Usually in such a light control panel, it is possible to block the visual field by controlling transmission and scattering of light by application or non-application of a voltage, but light cannot be blocked, with the result that the degree of glare tends to increase by light scattering. Then, for the purpose of reducing glare and improving contrast, etc., attempts have been made to use a dye as a material for a light control panel. For example, in the case of using such a light control panel for window glass of automobiles, it is required that the panel provides a good field of vision at a transparent state without cloudiness and provides high contrast. In addition, it is required that the panel has light resistance so as not to reduce transmittance by influence of long-term exposure outside even in the case of light irradiation at high temperatures for a long time. In addition, from the aspects of practicality and design, demand for a black element capable of blocking visible light has been increased.

To satisfy the above market demands, a wide variety of liquid crystal display elements called GH (guest host) type using liquid crystal compositions containing a dye have been proposed. These liquid crystal displays having characteristic viewing angles and brightness, have been put into practical use as vehicle applications and light control elements.

A dichroic dye commonly used in liquid crystal compositions for light control elements is required to have not only high contrast as the element but also light resistance, UV resistance, heat resistance, and compatibility (solubility) with components constituting a liquid crystal composition. Furthermore, to obtain a high-contrast black light control element, it is desired to develop a red dye having maximum absorption in the range of 500 to 550 nm which is a wavelength region with high luminosity factor and providing high contrast when used in a light control element in addition to the above requirements. Attempts have been made to improve these requisite properties. For example, Patent Literatures 4 to 6 disclose dichroic dyes having a maximum absorption wavelength in the range of 500 to 550 nm. However, the light control elements using the dyes disclosed in the literatures are insufficient in contrast. A dichroic dye having a maximum absorption wavelength in the above range and providing excellent contrast and light resistance for an element has not yet been found.

CITATION LIST

Patent Literature

PATENT LITERATURE 1: JP 63-501512 A
PATENT LITERATURE 2: JP 03-47392 A
PATENT LITERATURE 3: JP 2018-205746 A
PATENT LITERATURE 4: JP 2000-336366 A
PATENT LITERATURE 5: JP 2011-190314 A
PATENT LITERATURE 6: JP 2009-108295 A

SUMMARY OF INVENTION

Technical Problem

A first object of the present invention is to provide a novel anthraquinone compound.

Another object of the present invention is to provide a dichroic dye, which is a novel anthraquinone compound having a maximum absorption wavelength in a predetermined wavelength range, a liquid crystal composition containing the dichroic dye, and a light control element containing the composition and having excellent contrast and light resistance.

Solution to Problem

The present inventors have succeeded in obtaining a novel anthraquinone compound having a specific structure.

Furthermore, the present inventors have found that a light control element excellent in contrast and light resistance can be obtained using this novel anthraquinone compound having a maximum absorption wavelength in a predetermined wavelength range.

More specifically, aspects or embodiments encompassed within the present invention are as follows.

[1]. An anthraquinone compound represented by the following formula (1):

(1)

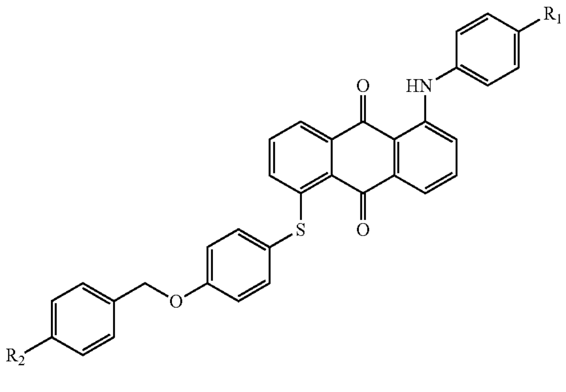

wherein $R_1$ represents a hydrogen atom, a linear or branched alkyl group having 1 to 12 carbon atoms, or a linear or branched alkoxy group having 1 to 12 carbon atoms, and $R_2$ represents a hydrogen atom, a linear or branched alkyl group having 1 to 8 carbon atoms, or a linear or branched alkoxy group having 1 to 8 carbon atoms.

[2]. The anthraquinone compound according to [1], wherein $R_2$ is a linear or branched alkyl group having 1 to 8 carbon atoms or a linear or branched alkoxy group having 1 to 4 carbon atoms.

[3]. The anthraquinone compound according to [2], wherein $R_2$ is a linear or branched alkyl group having 1 to 4 carbon atoms.

[4]. The anthraquinone compound according to [3], wherein $R_2$ is a branched alkyl group having 3 or 4 carbon atoms.

[5]. The anthraquinone compound according to any one of [1] to [4], wherein $R_1$ is a linear or branched alkoxy group having 1 to 8 carbon atoms.

[6]. The anthraquinone compound according to [5], wherein $R_1$ is a linear or branched alkoxy group having 5 to 8 carbon atoms.

[7]. The anthraquinone compound according to any one of [1] to [4], wherein $R_1$ is a linear or branched alkyl group having 4 to 10 carbon atoms.

[8]. The anthraquinone compound according to [7], wherein $R_1$ is a linear alkyl group having 5 to 8 carbon atoms.

[9]. The anthraquinone compound according to any one of [1] to [8], having a maximum absorption wavelength in 500 to 550 nm.

[10]. A light control liquid crystal composition comprising the anthraquinone compound according to any one of [1] to [9] and a liquid crystal material.

[11]. The light control liquid crystal composition according to [10], further comprising a dye compound other than the anthraquinone compound represented by formula (1).

[12]. The light control liquid crystal composition according to [10] or [11], further comprising a photocurable compound and a photopolymerization initiator.

[13]. A photocured product of the light control liquid crystal composition according to [12].

[14]. A light control element obtained by sandwiching the light control liquid crystal composition according to [10] or [11] or the photocured product according to [13] between a pair of substrates disposed facing each other, at least one of which is a transparent substrate having a transparent electrode.

[15]. The light control element according to [14], wherein both of the pair of the substrates are transparent substrates having a transparent electrode.

Advantageous Effects of Invention

The anthraquinone compound of the present invention having a maximum absorption wavelength in a predetermined wavelength range is excellent in light resistance and use of a light control liquid crystal composition containing the anthraquinone compound can provide a light control element excellent in contrast and light resistance.

DESCRIPTION OF EMBODIMENTS

The present invention will be described in detail, below.

The anthraquinone compound of the present invention is represented by the following formula (1):

(1)

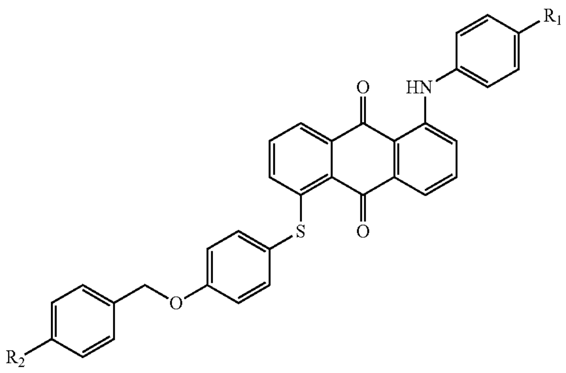

In formula (1), $R_1$ represents a hydrogen atom, a linear or branched alkyl group having 1 to 12 carbon atoms or a linear or branched alkoxy group having 1 to 12 carbon atoms.

The alkyl group having 1 to 12 carbon atoms and represented by $R_1$ in formula (1) may be either linear or branched. Examples of the alkyl group include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, a nonyl group, a decyl group, an undecyl group, a dodecyl group, a 2-ethylhexyl group, a 2-propylhexyl group, a 2-butylhexyl group, a 2-pentylhexyl group, and 2-pentylheptyl group. The carbon atoms of the linear alkyl group are preferably 4 to 10 and more preferably 5 to 8. The carbon atoms of the branched alkyl group are preferably 3 to 6 and more preferably 3 or 4.

The alkoxy group having 1 to 12 carbon atoms and represented by $R_1$ in formula (1) may be either linear or branched. Examples of the alkoxy group include a methoxy group, an ethoxy group, a n-propoxy group, an iso-propoxy group, a n-butoxy group, an iso-butoxy group, a sec-butoxy group, a t-butoxy group, a n-pentyloxy group, an iso-pentyloxy group, a neo-pentyloxy group, a t-pentyloxy group, a hexyloxy group, a heptyloxy group, an octyloxy group, a nonyloxy group, a decyloxy group, an undecyloxyl group, a dodecyloxy group, a 2-ethylhexyloxy group, a 2-propylhexyloxy group, a 2-butylhexyloxy group, a 2-pentylhexyloxy group, and 2-pentylheptyloxy group. A linear or branched alkoxy group having 1 to 8 carbon atoms is preferable and a linear or branched alkoxy group having 5 to 8 carbon atoms is more preferable. A linear alkoxy group having 5 to 8 carbon atoms is further preferable.

In formula (1), $R_1$ preferably represents a linear alkyl group having 1 to 10 carbon atoms, a branched alkyl group having 3 to 6 carbon atoms, or a linear or branched alkoxy group having 1 to 8 carbon atoms. A linear alkyl group having 4 to 10 carbon atoms, a branched alkyl group having 3 or 4 carbon atoms, or a linear or branched alkoxy group having 5 to 8 carbon atoms are more preferable. A linear alkyl group having 5 to 8 carbon atoms or a linear alkoxy group having 5 to 8 carbon atoms is further preferable.

In formula (1), $R_2$ represents a hydrogen atom, a linear or branched alkyl group having 1 to 8 carbon atoms, or a linear or branched alkoxy group having 1 to 8 carbon atoms.

The alkyl group having 1 to 8 carbon atoms and represented by $R_2$ in formula (1) may be either linear or branched. Examples of the alkyl group include a methyl group, an ethyl group, a n-propyl group, an iso-propyl group, a n-butyl group, an iso-butyl group, a sec-butyl group, a t-butyl group, a n-pentyl group, an iso-pentyl group, a neo-pentyl group, a t-pentyl group, a hexyl group, a heptyl group, an octyl group, and a 2-ethylhexyl group. A linear or branched alkyl group having 1 to 4 carbon atoms is preferable and a branched alkyl group having 3 or 4 carbon atoms is more preferable.

The alkoxy group having 1 to 8 carbon atoms and represented by $R_2$ in formula (1) may be either linear or branched. Examples of the alkoxy group include a methoxy group, an ethoxy group, a n-propoxy group, an iso-propoxy group, a n-butoxy group, an iso-butoxy group, a sec-butoxy group, a t-butoxy group, a n-pentyloxy group, an iso-pentyloxy group, a neo-pentyloxy group, a t-pentyloxy group, a hexyloxy group, a heptyloxy group, an octyloxy group, and a 2-ethylhexyloxy group. A linear or branched alkoxy group having 1 to 4 carbon atoms is more preferable. A linear alkoxy group having 1 to 4 carbon atoms is further preferable.

In formula (1), $R_2$ is preferably a linear or branched alkyl group having 1 to 8 carbon atoms or a linear or branched alkoxy group having 1 to 4 carbon atoms. A linear or branched alkyl group having 1 to 4 carbon atoms or a linear alkoxy group having 1 to 4 carbon atoms is more preferable; a linear or branched alkyl group having 3 or 4 carbon atoms is further preferable; and a branched alkyl group having 3 or 4 carbon atoms is furthermore preferable.

Preferable specific examples of the compound represented by formula (1) are shown below but the present invention is not limited to these.

No. 1

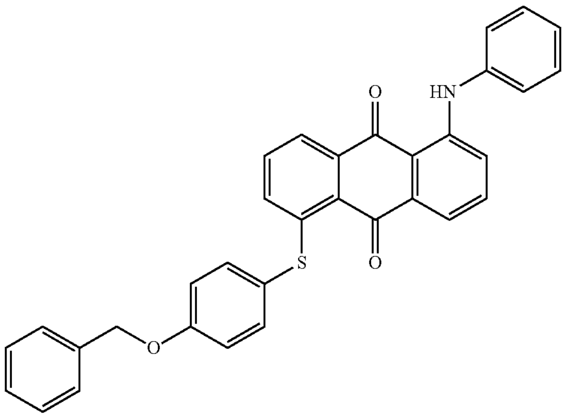

No. 2

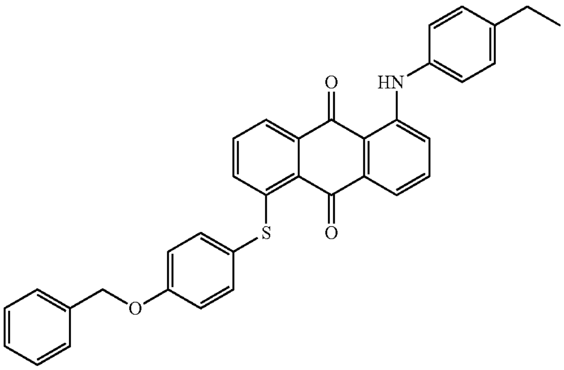

No. 3

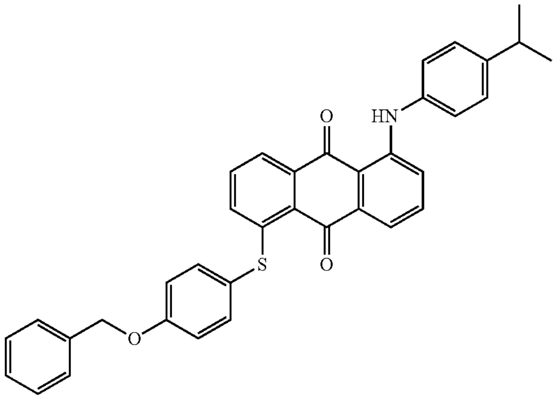

No. 4

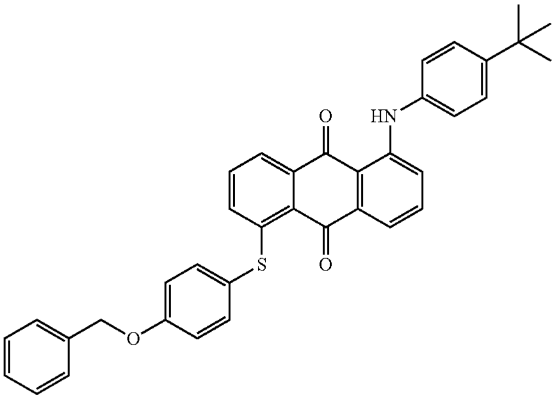

No. 5

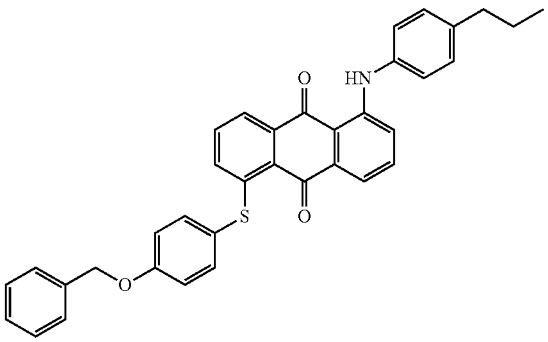

No. 6

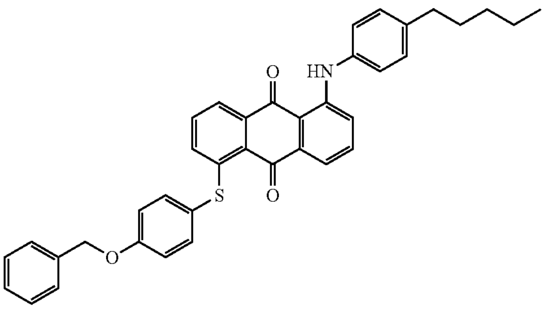

-continued
No. 7
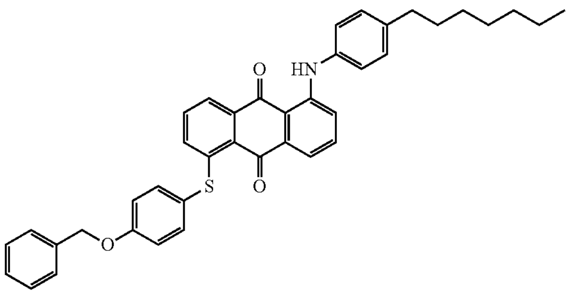
No. 8
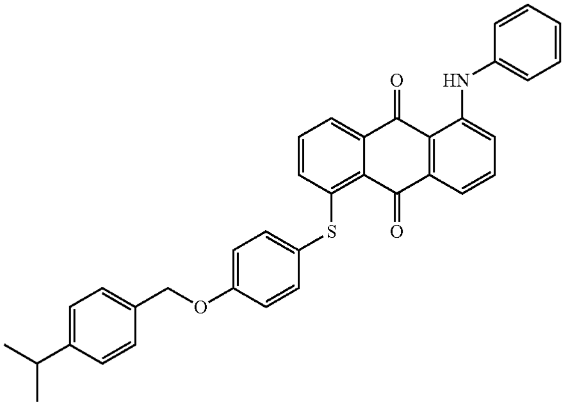
No. 9
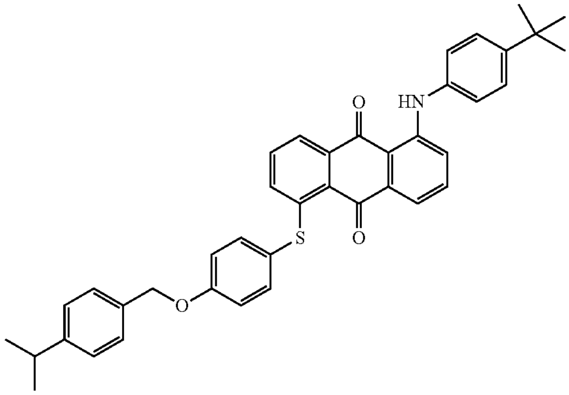
No. 10
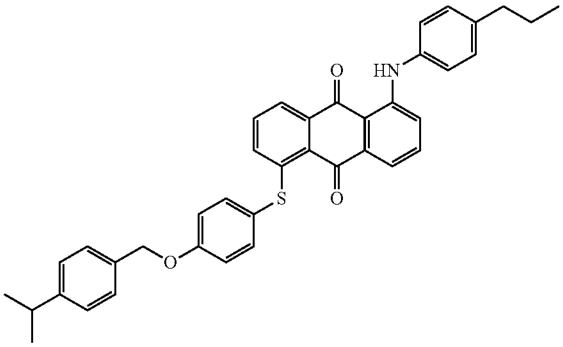
No. 11
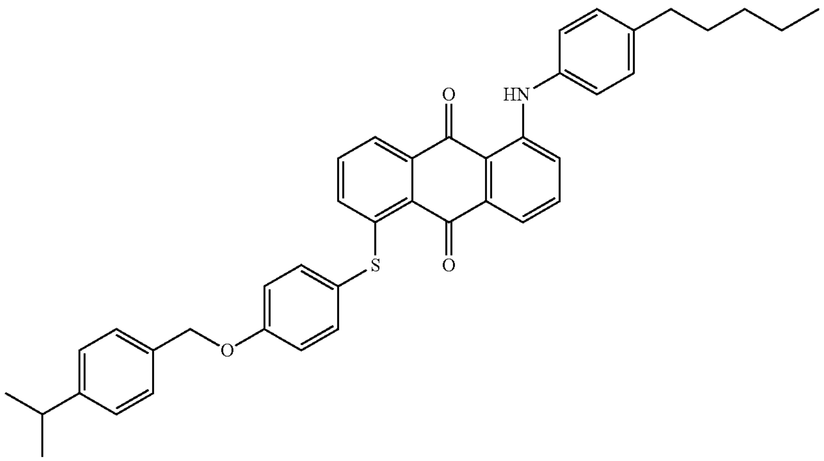

-continued
No. 12
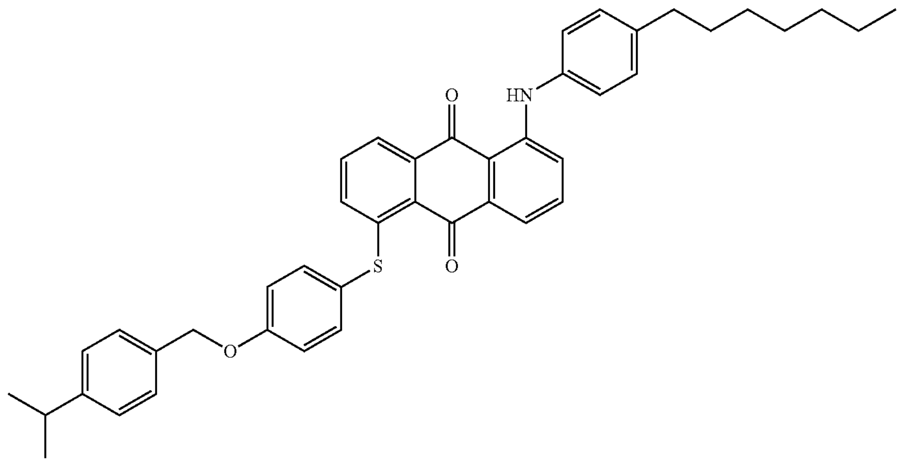
No. 13
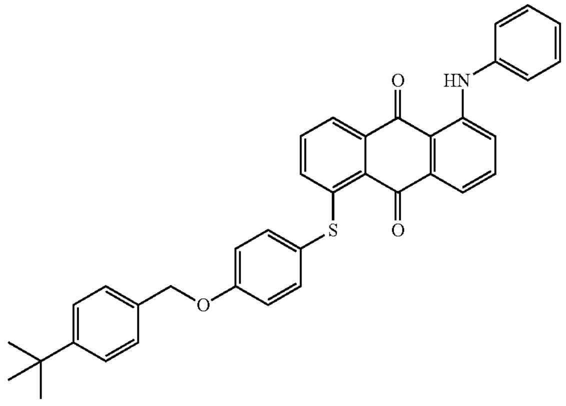
No. 14
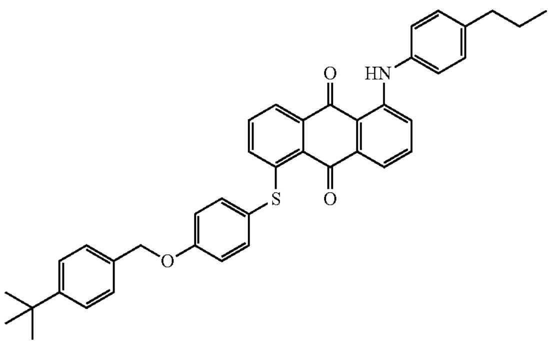
No. 15
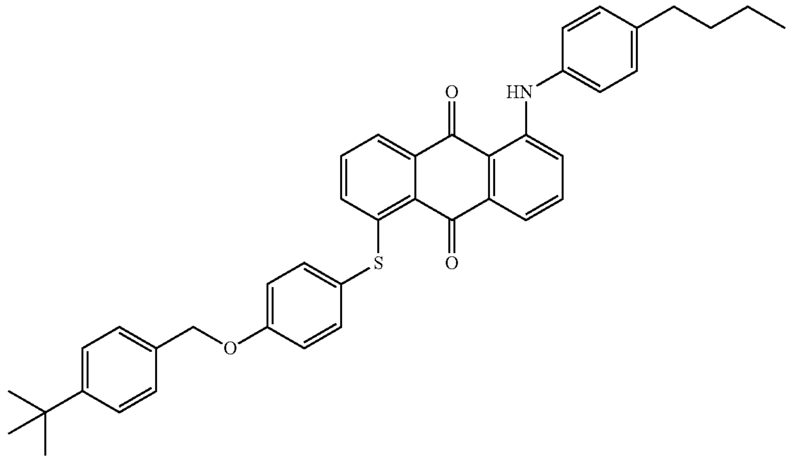

-continued
No. 16
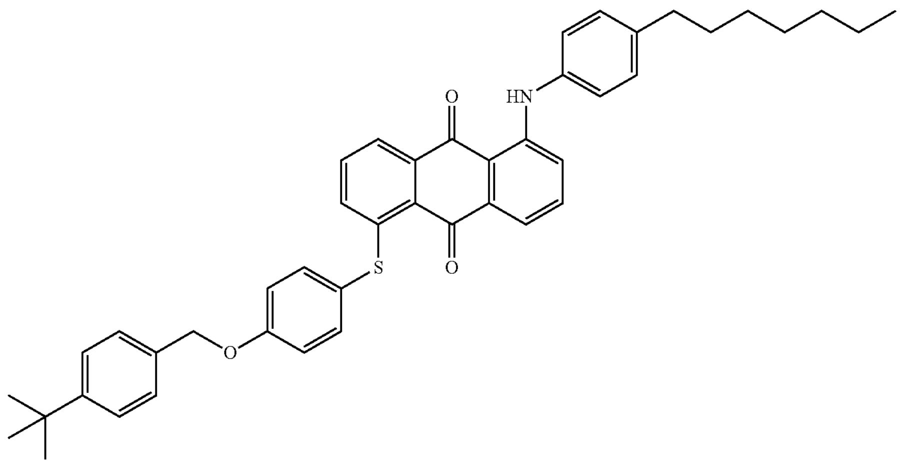
No. 17
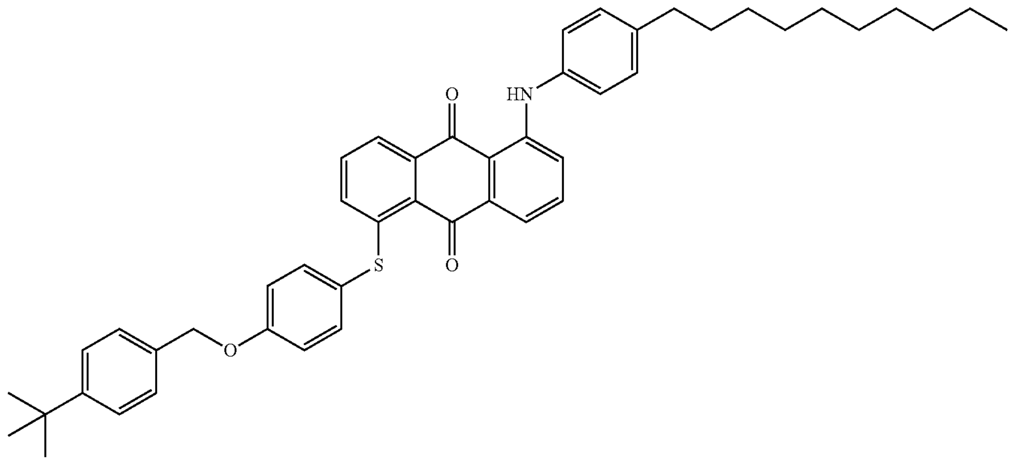
No. 18
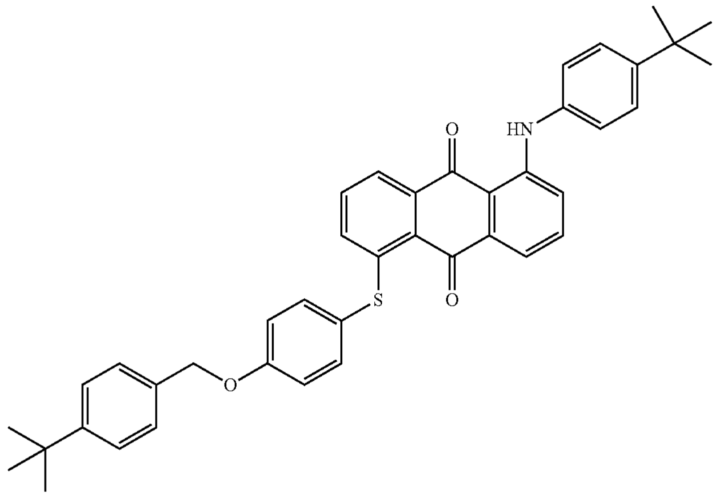

-continued
No. 19
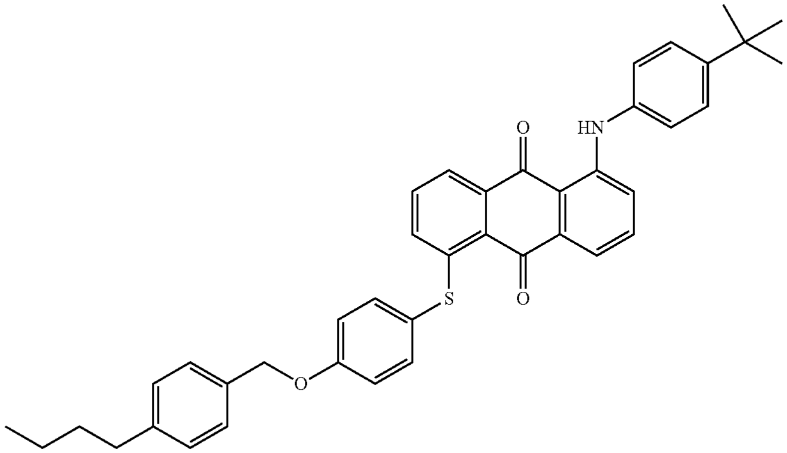
No. 20
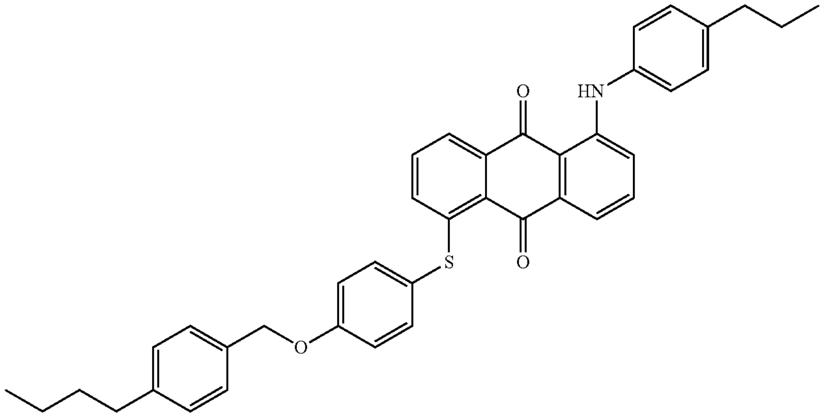
No. 21
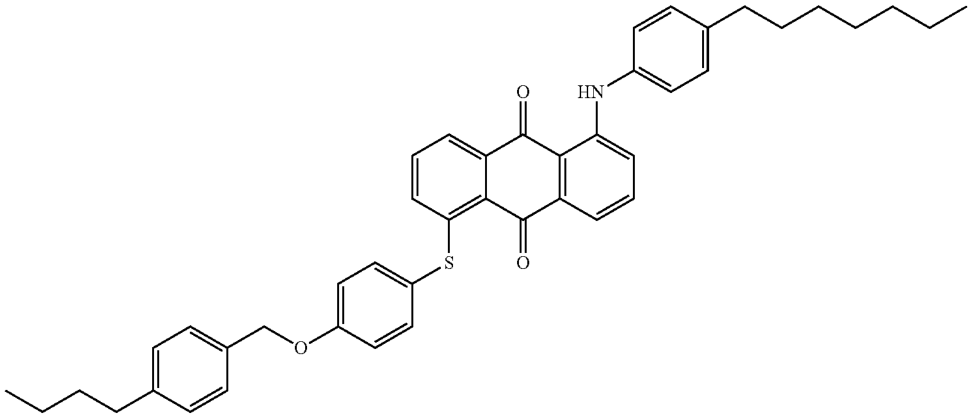

-continued
No. 22
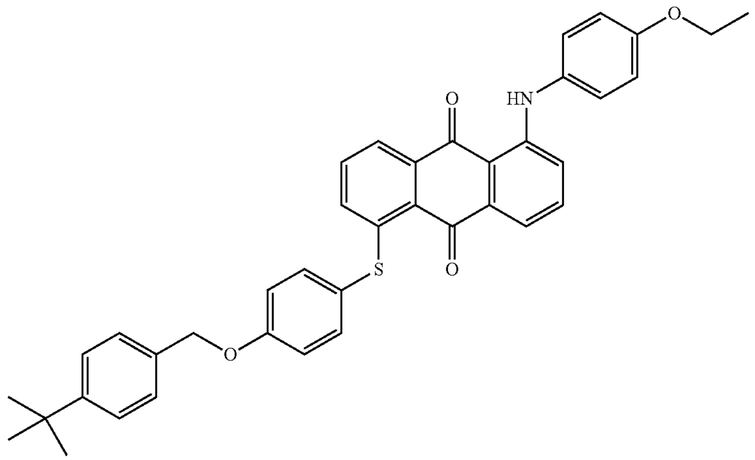
No. 23
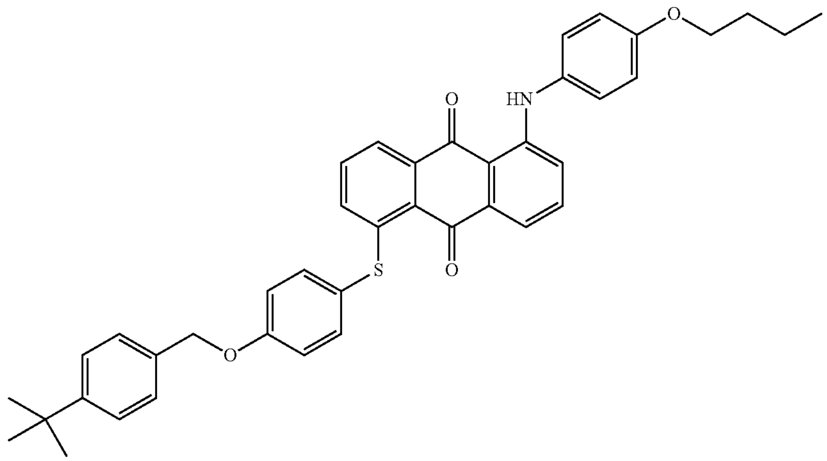
No. 24
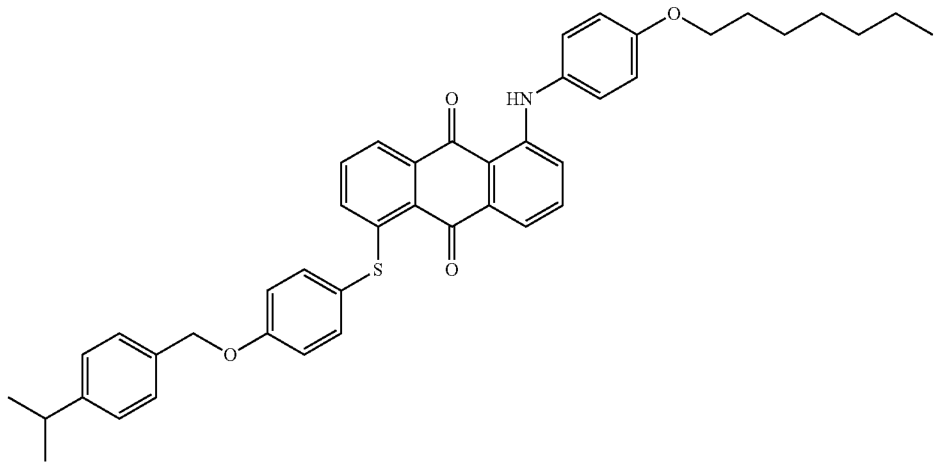

-continued
No. 25
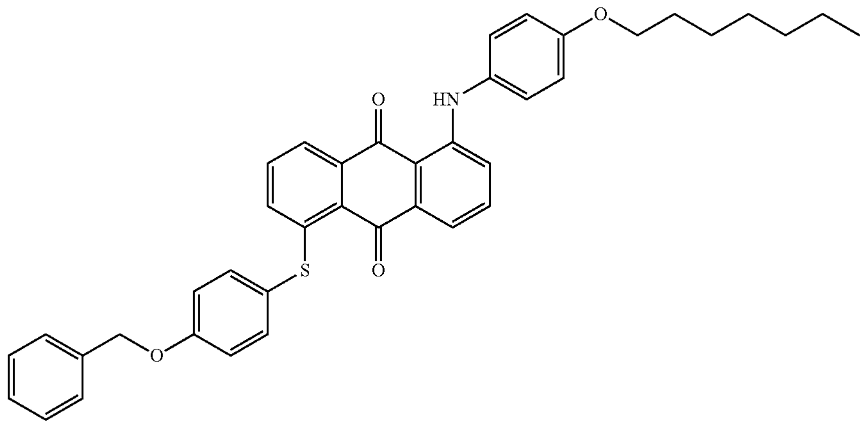
No. 26
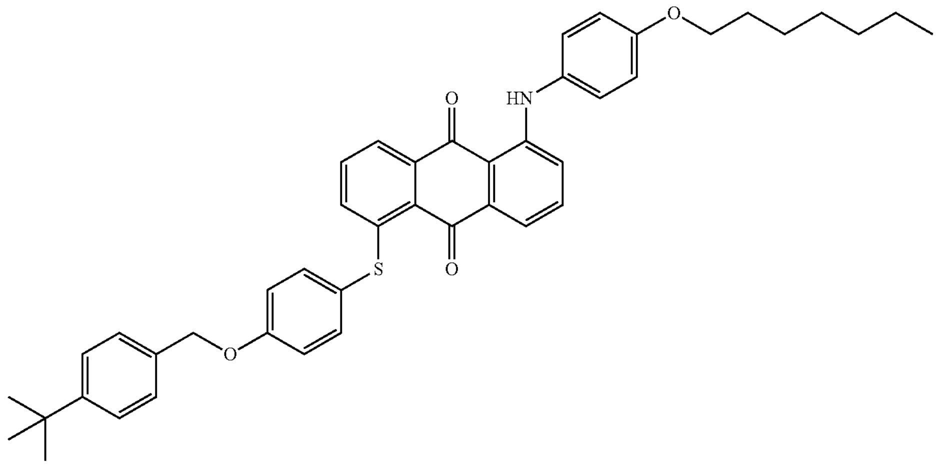
No. 27
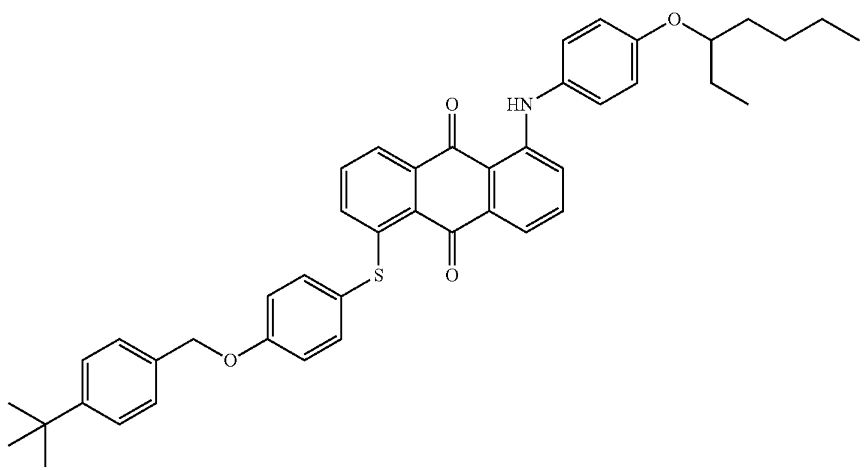

-continued
No. 28
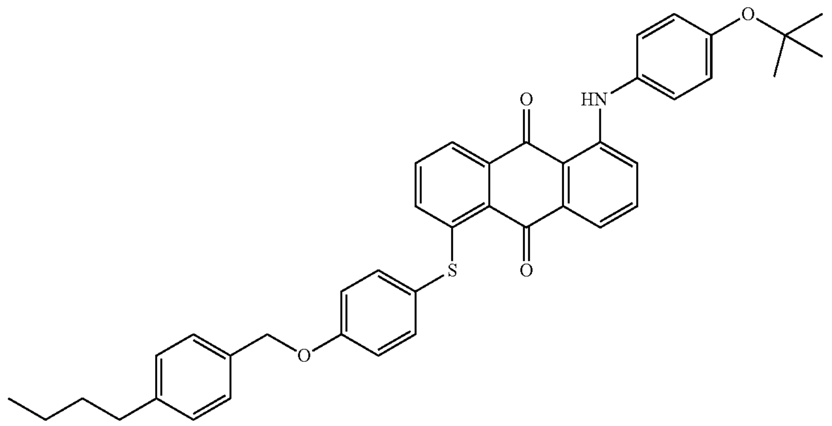
No. 29
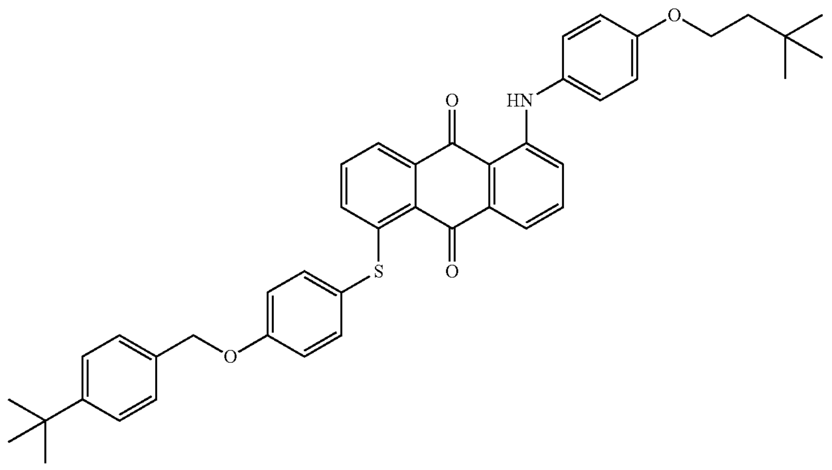
No. 30
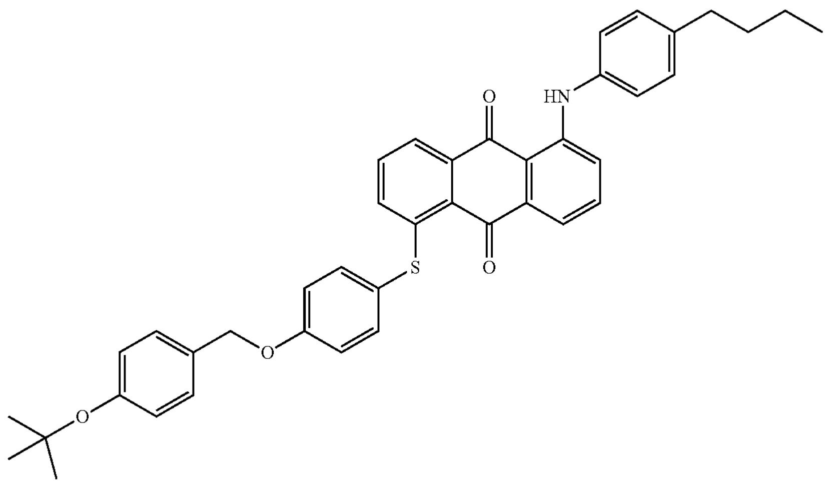

-continued
No. 31
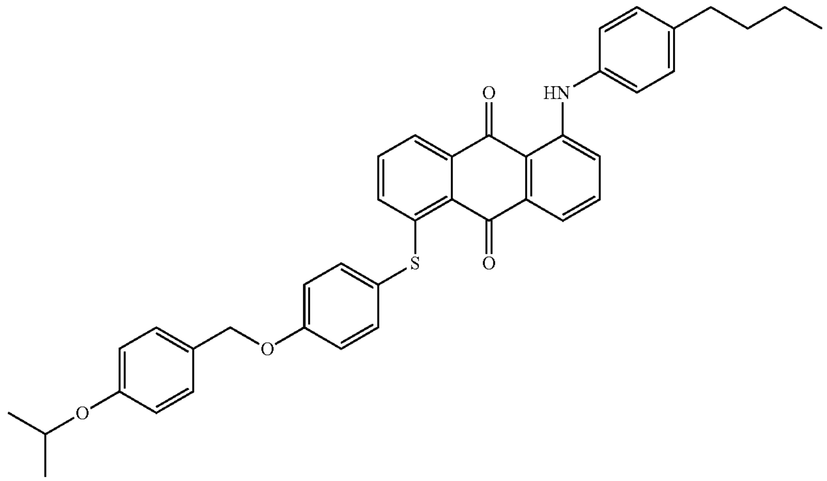
No. 32
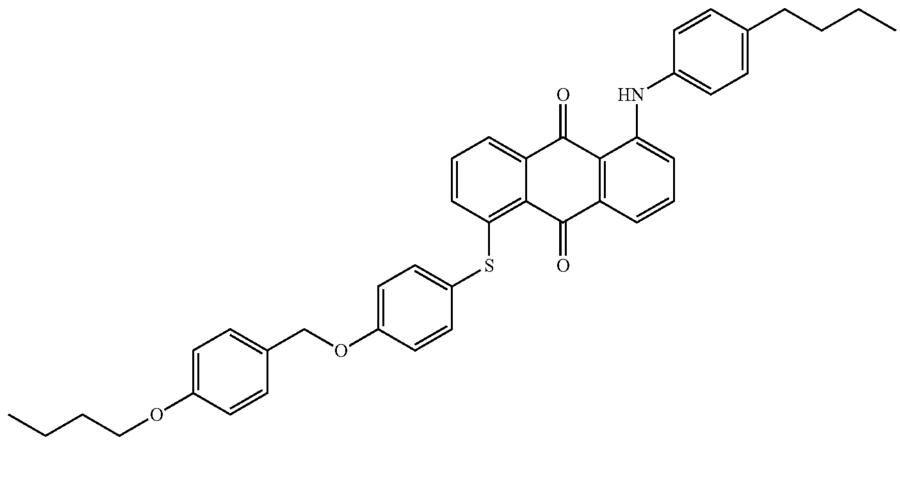
No. 33
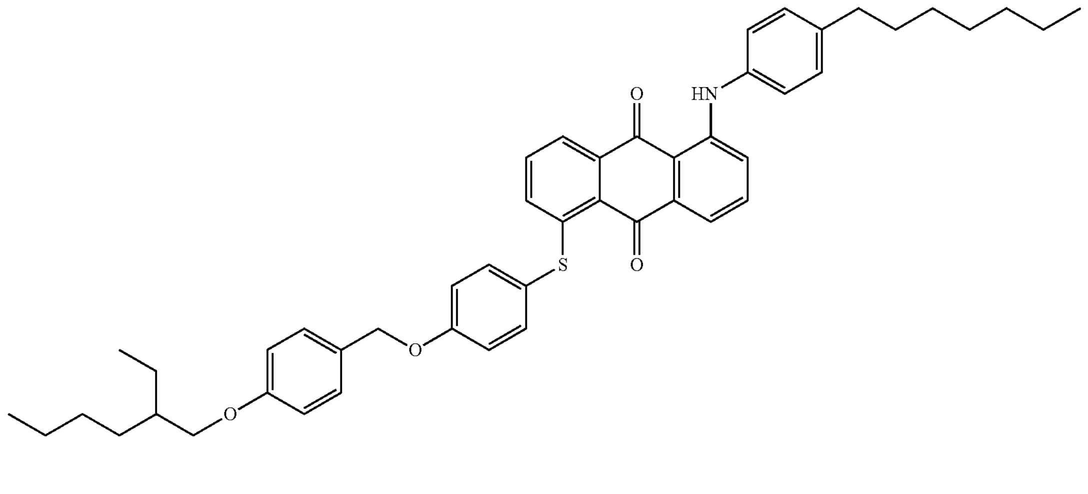

-continued

No. 34

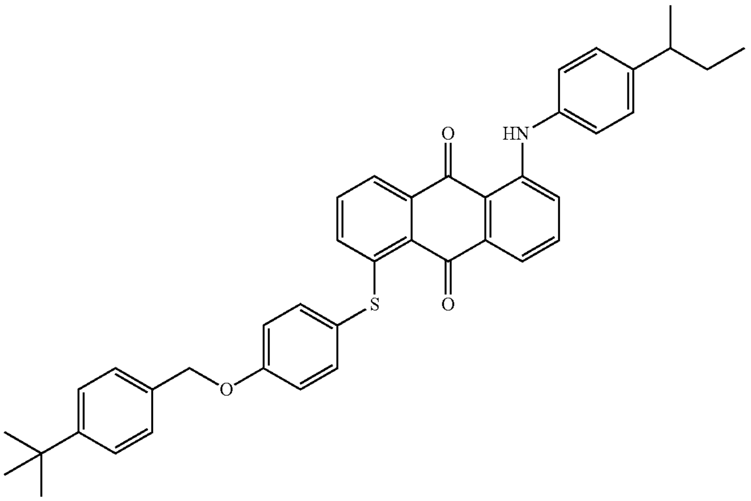

The compound represented by formula (1) preferably has a maximum absorption wavelength in the range of 500 to 550 nm. Furthermore, the compound represented by formula (1) is preferably a compound exhibiting a transmittance difference of 43% or more when formed into an element. Furthermore, the compound represented by formula (1) is preferably a compound having a maximum absorption wavelength in the range of 500 to 550 nm and exhibiting a transmittance difference of 43% or more when formed into an element. Use of a liquid crystal composition containing the compound having a maximum absorption wavelength in the aforementioned range and/or a high transmittance difference in a light control element improves the contrast of the light control element.

The compound represented by formula (1) can be synthesized by using a method conventionally known in the technical field, for example, disclosed in JP 2003-192664 A.

More specifically, the compound represented by formula (1) can be synthesized, for example, by reacting a 1,5-dichloroanthraquinone compound and an aniline derivative represented by the following formula (A) in the presence of a catalyst such as palladium or copper powder, under a basic condition of e.g., tripotassium phosphate in a solvent such as xylene at 110 to 120° C. followed by reacting with a thiol represented by the following formula (B) under a basic condition at 50 to 60° C., and then, reacting with a benzyl chloride derivative represented by the following formula (C) under a basic condition at 70 to 80° C. It is noted that $R_1$ in the following formula (A) and $R_2$ in the formula (C) are defined the same as $R_1$ and $R_2$ in formula (1).

(A)

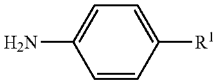

(B)

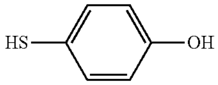

-continued (C)

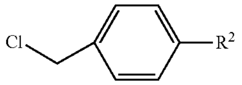

The liquid crystal composition of the present invention (hereinafter sometimes referred to simply as "the composition of the present invention") contains the anthraquinone compound represented by formula (1) and a liquid crystal material.

The content of the anthraquinone compound represented by formula (1) in the liquid crystal composition is not particularly limited but preferably 0.5 to 10 parts by mass relative to 100 parts by mass of a liquid crystal material and more preferably 0.5 to 5 parts by mass. In the case where a dichroic dye (described later) other than the compound represented by formula (1) is used in combination, it is preferable that the total content of the anthraquinone compound represented by formula (1) and a dichroic dye other than the compound represented by formula (1) falls within the aforementioned range (0.5 to 10 parts by mass) relative to 100 parts by mass of a liquid crystal material.

The liquid crystal material to be contained in the liquid crystal composition of the present invention is not particularly limited as long as it is a material having a liquid crystallinity (i.e., a compound having liquid crystallinity), such as a nematic liquid crystal, a cholesteric liquid crystal and a smectic liquid crystal. Among them, a nematic liquid crystal is preferable. Examples of the compound having liquid crystallinity include liquid crystal compounds disclosed in, for example, "Liquid Crystal Device Handbook" (edited by the 142nd Committee of Japan Society for the Promotion of Science, Nikkan Kogyo Shimbunsha, 1989), pages 154 to 192 and pages 715 to 722.

The liquid crystal composition of the present invention may contain a dichroic dye other than the anthraquinone compound represented by formula (1) or an optically active substance showing or not showing liquid crystallinity, such as cholesteryl nonanoate, additives such as a UV absorber and an antioxidant, a photocurable compound, and a photopolymerization initiator, etc.

The photocurable compound that can be contained in the liquid crystal composition of the present invention is not particularly limited as long as it is a compound having a functional group polymerizable by the function of a photopolymerization initiator (described later) upon light irradiation. Examples of the photocurable compound include a compound having a (meth)acrylate group, a compound having a vinyl group, and a compound having an allyl group. A compound having a (meth)acrylate group is preferable. Note that, the wording "(meth)acrylate" in the specification means "methacrylate and/or acrylate".

Examples of the (meth)acrylate compound to be contained in the liquid crystal composition of the present invention include, but are not limited to, mono(meth)acrylate compounds having a single (meth)acrylate group in one molecule and di(meth)acrylate compounds having two (meth)acrylate groups in one molecule.

As the mono(meth)acrylate compound, a mono(meth) acrylate having a linear, circular or branched alkyl group having 5 to 13 carbon atoms is preferable. Examples of the mono(meth)acrylate compound include, linear alkyl mono (meth)acrylates such as pentyl (meth)acrylate, hexyl (meth) acrylate, heptyl (meth)acrylate, octyl (meth)acrylate, nonyl (meth)acrylate, decyl (meth)acrylate, undecyl (meth)acrylate, dodecyl (meth)acrylate, and tridecyl (meth)acrylate; cyclic alkyl mono(meth)acrylates such as isobornyl (meth) acrylate; and branched alkyl mono(meth)acrylates such as 2-methylhexyl (meth)acrylate, 2-ethylhexyl (meth)acrylate, 2-propylhexyl (meth)acrylate, 2-methylheptyl (meth)acrylate, 2-ethylheptyl (meth)acrylate, and 2-propylheptyl (meth)acrylate.

Examples of the di(meth)acrylate compound include, 1,4-butanediol di(meth)acrylate, 1,5-pentanediol di(meth) acrylate, 1,6-hexanediol di(meth)acrylate, 1,7-heptanediol di(meth)acrylate, 1,8-octanediol di(meth)acrylate, 1,9-nonanediol di(meth)acrylate, 1,10-decanediol di(meth)acrylate, 1,11-undecanediol di(meth)acrylate, 1,12-dodecanediol di(meth)acrylate, and 1,13-tridecanediol di(meth)acrylate, and further, trialkylene glycol di(meth)acrylate such as triethylene glycol di(meth)acrylate.

In the liquid crystal composition of the present invention, a mono(meth)acrylate compound and a di(meth)acrylate compound may be used in combination. In the case where a mono(meth)acrylate compound and a di(meth)acrylate compound are used in combination, the mass ratio of the mono(meth)acrylate compound to di(meth)acrylate compound is preferably 10:90 to 96:4 and more preferably 50:50 to 95:5.

The photopolymerization initiator that can be contained in the composition of the present invention is not particularly limited as long as it is a compound capable of polymerizing a photocurable compound by light irradiation. The photopolymerization initiator is preferably one that does not remain in the cured product after light irradiation and does not cause deterioration of the dichroic dye such as the anthraquinone compound represented by formula (1) in the cured product.

As the photopolymerization initiator, alkylphenone photopolymerization initiators such as Darocure 1173, Irgacure 651, and Irgacure 184; and phosphine oxide photopolymerization initiators such as Irgacure TPO are preferably used.

In the case where the composition of the present invention contains a photocurable compound and a photopolymerization initiator, the ratio (by mass) of the total amount of the anthraquinone compound represented by formula (1) and liquid crystal material to the amount of the photocurable compound in the composition is preferably 90:10 to 50:50, more preferably 80:20 to 50:50, and further preferably 65:35 to 50:50. If the ratio of the photocurable compound falls within the above range, it is possible to prevent separation of the liquid crystal material and the photocurable compound before curing by light irradiation and also prevent decrease in the light blocking effect of a cured product.

It is noted that, in the case where a dichroic dye (described later) other than the compound represented by formula (1) is used in combination, the ratio of the total amount of all dichroic dyes including the anthraquinone compound represented by formula (1) and a liquid crystal material to the amount of a photocurable compound in the composition of the present invention preferably falls within the above range (i.e., the mass ratio of 90:10 to 50:50). The more preferable range and further preferable range thereof are the same as those specified above.

In the case of containing a photocurable compound and a photopolymerization initiator, the content of the photopolymerization initiator in the composition of the present invention is preferably 0.1 to 5 parts by mass relative to 100 parts by mass of the photocurable compound.

In the composition of the present invention, a dichroic dye other than the anthraquinone compound represented by formula (1) can be used in combination.

The dichroic dye that can be used in combination is not particularly limited and may be selected from, e.g., an azo dye, an anthraquinone dye, a perylene dye, a quinophthalone dye, a merocyanine dye, an azomethine dye, a phthaloperylene dye, an indigo dye, an azulene dye, a dioxazine dye, and a polythiophene dye. More specifically, dyes disclosed in "Dichroic dyes for Liquid Crystal Display" (written by A. V. Ivashchenko, company: CRC, 1994) can be mentioned.

Among them, an azo dye, an anthraquinone dye, a perylene dye, or a quinophthalone dye is preferably used in combination, and an azo dye or an anthraquinone dye is more preferably used in combination.

In the case of using a dichroic dye other than the anthraquinone compound represented by formula (1) in combination, the content of the anthraquinone compound represented by formula (1) in all dichroic dyes is not particularly limited as long as the effect of the present invention is not impaired. The content rate thereof is preferably 1 to 80 mass %, more preferably 5 to 70 mass %, and further preferably 10 to 50 mass %.

The composition of the present invention may further contain a light stabilizer such as a benzotriazole based light stabilizer, a benzophenone based light stabilizer, or a hindered amine based light stabilizer; an antioxidant such as a phosphite based antioxidant and a hindered phenol based antioxidant; a thermal polymerization inhibitor, a thiol compound, a photo-sensitizer, a photosensitizer, a chain transfer inhibitor, a polymerization inhibitor, an adhesion imparting agent, an antifoaming agent, a crosslinking agent, a surfactant, a heat curing accelerator, a thermoplastic resin, thermosetting resin, a thickener such as urethane diacrylate, or the like, in addition to the aforementioned components.

Also, to control a cell gap in the use for light control element, a spherical or cylindrical spacer such as silica, glass, plastic or ceramic may be added to the composition. The cell gap herein can be set to fall within the range of 2 to 100 μm.

The composition of the present invention can be obtained by mixing and stirring the anthraquinone compound represented by formula (1) and the liquid crystal material, which are essential components, and other optional components such as a photocurable compound and a photopolymerization initiator which may be added if necessary. The mixing and stirring may be most simply performed by putting all components in a container and just manually stirring them but it is effective to stir the components by use of a device such as a magnetic stirrer. To efficiently prepare a uniform composition, it is preferable that a uniform mixture of a photocurable compound, a photopolymerization initiator, and a liquid crystal material is firstly prepared, and then, the anthraquinone compound represented by formula (1) and optional components are added thereto and stirred. During stirring and mixing, heating may be performed, if necessary, but stirring and mixing are preferably performed in a short time as much as possible under a light source emitting light having an absorption wavelength of a photopolymerization initiator. After individual components are mixed, the mixture may be further filtered by a mesh, a membrane filter or the like.

When the composition of the present invention containing a photocurable compound and a photopolymerization initiator is irradiated with light, a cured product of the liquid crystal composition, in which the photocurable compound component is cured (polymerized), can be obtained. It is noted that the "photocured product" in the present invention refers to the state where a functional group of a photocurable compound is polymerized or copolymerized by light irradiation and does not necessarily mean a cured product in which the anthraquinone compound represented by formula (1) and a liquid crystal material, or the like has contributed to the curing reaction.

The light source for light irradiation is not particularly limited as long as it is a light source capable of emitting light having a wavelength absorbed by a photopolymerization initiator. Examples of a preferable light source include light sources that can emit ultraviolet light rays such as a high-pressure mercury lamp, a metal halide lamp, a xenon lamp, and a halogen lamp.

The light control element of the present invention is obtained by sandwiching a layer of the liquid crystal composition or a photocured product thereof between a pair of substrates disposed facing each other at least one of which is a transparent substrate having a transparent electrode. Examples of the substrate herein include substrates made of an inorganic transparent material such as glass or quartz; and substrates made of a colorless and transparent or colored transparent or opaque material such as a metal, a metal oxide, a semiconductor, ceramics, a plastic plate, or a plastic film. The electrode is a thin film formed of, e.g., a metal oxide, a metal, a semiconductor, or an organic conductive material on the entire or part of the surface of the substrate by, e.g., a coating method or printing method known in the art or a vapor deposition method such as sputtering. Particularly, to form a light control element having a large area, it is desirable to use an electrode substrate having an ITO (indium oxide, tin oxide) electrode formed on a transparent polymer film such as PET by a vapor deposition method such as sputtering or a printing method, from the viewpoint of productivity and processability. In a more preferable embodiment, both of the pair of substrates are transparent substrates having a transparent electrode. It is noted that wiring may be provided on the substrates for connecting the electrodes with each other or connecting the electrodes and the outside. For example, an electrode substrate for driving a segment, an electrode substrate for driving a matrix, or an electrode substrate for driving an active matrix may be used. Furthermore, the surface of the electrode formed on the substrate may be entirely or partially covered with a protective film or alignment film formed of an organic compound such as a polyimide, polyamide, silicone, or cyan compound, an inorganic compound such as $SiO_2$, $TiO_2$, or $ZrO_2$, or a mixture of these.

A flexible and light-weight light control element can be obtained by using a plastic film as a substrate. Because of this, a light control element can be used by sandwiching it between a pair of, e.g., planar or curved glass or hard plastic, via an adhesive layer formed of, e.g., polyvinyl butyral, vinyl acetate, a double-sided tape, or an adhesive agent. Alternatively, a light control element can be used by bonding it to, e.g., a single planar or curved glass or hard plastic substrate with, e.g., a double-sided tape or an adhesive agent. Alternatively, a light control element may be sandwiched between soft plastic substrates or bonded on one or both surfaces thereof. Alternatively, a protective layer such as a hard coat, a UV-cut layer, an infrared-cut layer, or a half mirror may be provided; a color filter may be laminated; or a polarized filter may be attached onto the surface of a substrate opposite to the electrode surface of a light control element. Alternatively, a light control element may be laminated together with an electroluminescent display element, a light emitting diode display element, an electrochromic display element, or another liquid crystal display element.

A drive unit for applying a voltage to the light control element of the present invention may be a unit capable of applying a direct-current voltage of 2 to 100 V or an alternating-current voltage of 10 to 1000 Hz, and causing an open circuit or short circuit between electrodes when no voltage is applied. Furthermore, the drive unit may be equipped with, e.g., a voltage application circuit for driving a segment, a voltage application circuit for driving a matrix, and a voltage application circuit for an active matrix.

The light control element using the anthraquinone compound represented by formula (1) of the present invention can realize high-contrast display. Furthermore, since the light control element has excellent light resistance during outdoor exposure for a long term, the light control element of the present invention is suitable for vehicle applications or building-material applications.

EXAMPLES

Hereinafter, the present invention will be described in more detail with reference to Examples, but the present invention is not limited to these.

The terms "part" and "%" in the text are on a mass basis unless otherwise specified. The maximum absorption wavelengths in Examples were measured with a spectrophotometer "UV-3150" manufactured by Shimadzu Corporation.

Example 1 (Synthesis of Anthraquinone Compound of Present Invention represented by No. 16 in Specific Compound Examples)

Step (1-1) Synthesis of Intermediate Compound Represented by the Following Formula (2)

To xylene (170 parts), 2,2-bis(diphenylphosphino)-1,1-binaphthyl (1.7 parts) and tris(dibenzylideneacetone)dipalladium (1.6 parts) were added. The mixture was stirred at 80° C. for 10 minutes under a nitrogen atmosphere. Thereafter, 1,5-dichloroanthraquinone (10.0 parts), tripotassium phosphate (11.5 parts), 4-heptylaniline (10.3 parts) and N-methyl-2-pyrrolidone (34 parts) were added thereto, which was followed by stirring the reaction liquid at 120° C. for 12 hours. The reaction liquid was cooled to 45° C. and then methanol (340 parts) was added thereto and stirred for 30 minutes. The reaction product was collected by filtration, stirred in toluene (142 parts) and methanol (71 parts) for 30 minutes and then filtered. The filtrate was concentrated under reduced pressure. The resultant reaction product was dried at 80° C. by a hot-air dryer for 24 hours to obtain an intermediate compound (4.7 parts) represented by the following formula (2).

(2)

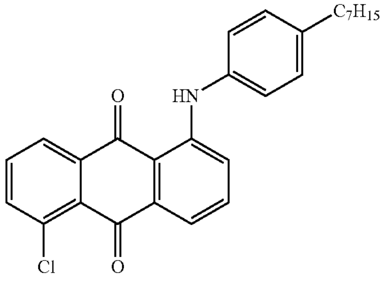

Step (1-2) Synthesis of Intermediate Compound Represented by the Following Formula (3)

To N,N-dimethylformamide (60 parts), the intermediate compound (4.6 parts) represented by formula (2) and obtained in step (1-1), potassium carbonate (5.1 parts) and 4-hydroxybenzenethiol (2.7 parts) were added. The mixture was stirred at 50° C. for one hour. After the reaction liquid was cooled to 30° C., methanol (129 parts) and water (92 parts) were added thereto, which was followed by stirring the reaction liquid for 20 minutes. The reaction product was obtained by filtration and dried by a hot air dryer of 80° C. for 24 hours to obtain an intermediate compound (4.4 parts) represented by the following formula (3).

(3)

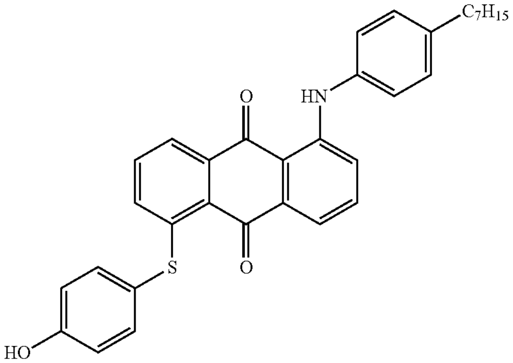

Step (1-3) Synthesis of Compound Represented by No. 16 in Specific Compound Examples To N-methyl-2-pyrrolidone (56 parts), the intermediate compound (4.4 parts) represented by formula (3) and obtained in step (1-2), potassium carbonate (2.3 parts) and 4-t-butylbenzyl chloride (2.3 parts) were added. The mixture was stirred at 80° C. for one hour and the reaction liquid was then cooled to 40° C. Thereafter, methanol (112 parts) was added thereto and the reaction solution was stirred for 20 minutes. The reaction product was collected by filtration and dried by a hot air dryer at 80° C. for 24 hours. The resultant crude product was dissolved in toluene and subjected to column purification using a developing solvent (toluene:hexane=2:1). After purification, the solvent was evaporated under reduced pressure from the solution and the resultant material was dried by a vacuum dryer of 50° C. for 24 hours to obtain the compound (2.9 parts) represented by No. 16 in the specific compound examples cited above as a red solid substance. The maximum absorption wavelength of the compound in methanol was 518 nm.

Example 2 (Synthesis of Anthraquinone Compound of Present Invention represented by No. 15 in Specific Compound Examples)

Step (2-1)

The compound (3.0 parts) represented by No. 15 in the specific compound examples cited above was obtained as a red solid substance in the same manner as in Example 1 except that 4-heptylaniline (10.3 parts) in step (1-1) was replaced with 4-butylaniline (8.1 parts). The maximum absorption wavelength of the compound in methanol was 513 nm.

Example 3 (Synthesis of Anthraquinone Compound of Present Invention represented by No. 17 in Specific Compound Examples)

Step (3-1)

The compound (3.0 parts) represented by No. 17 in the specific compound examples cited above was obtained as a red solid substance in the same manner as in Example 1 except that 4-heptylaniline (10.3 parts) in step (1-1) was replaced with 4-decylaniline (12.6 parts). The maximum absorption wavelength of the compound in methanol was 515 nm.

Example 4 (Synthesis of Anthraquinone Compound of Present Invention represented by No. 26 in Specific Compound Examples)

Step (4-1)

The compound (3.0 parts) represented by No. 26 in the specific compound examples cited above was obtained as a red solid substance in the same manner as in Example 1 except that 4-heptylaniline (10.3 parts) in step (1-1) was replaced with 4-heptyloxyaniline (11.2 parts). The maximum absorption wavelength of the compound in methanol was 515 nm.

Example 5 (Synthesis of Anthraquinone Compound of Present Invention represented by No. 32 in Specific Compound Examples)

Step (5-1)

The compound (3.0 parts) represented by No. 32 in the specific compound examples was obtained as a red solid substance in the same manner as in Example 1 except that 4-heptylaniline (10.3 parts) in step (1-1) was replaced with 4-butylaniline (8.1 parts) and 4-t-butylbenzyl chloride (2.3 parts) in step (1-3) was replaced with 1-butoxy 4-chloromethylbenzene (2.3 parts). The maximum absorption wavelength of the compound in methanol was 513 nm.

Example 6 (Synthesis of Anthraquinone Compound of Present Invention represented by No. 34 in Specific Compound Examples)

Step (6-1)

The compound (3.0 parts) represented by No. 34 in the specific compound examples cited above was obtained as a red solid substance in the same manner as in Example 1 except that 4-heptylaniline (10.3 parts) in step (1-1) was replaced with 4-sec-butylaniline (8.1 parts). The maximum absorption wavelength of the compound in methanol was 513 nm.

Comparative Example 1 (Synthesis of Compound of Comparative Example)

The compound (2.9 parts) represented by the following formula (X) was obtained as a red solid substance in the same manner as in Example 1 except that 4-heptylaniline (10.3 parts) in step (1-1) was replaced with 4-butylaniline (4.3 parts); 4-hydroxybenzenethiol (2.7 parts) in step (1-2) was replaced with 4-t-butylbenzenethiol (3.5 parts); and subsequent steps was not performed. The maximum absorption wavelength of the compound in methanol was 518 nm.

(X)

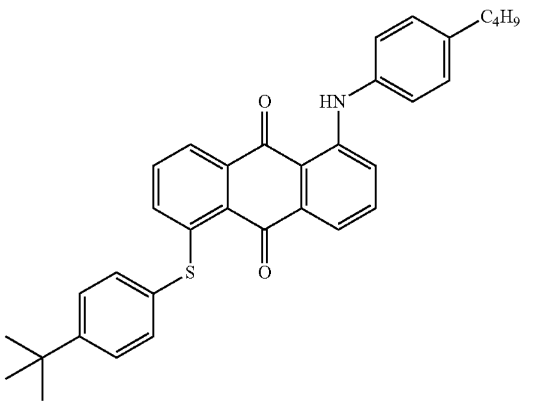

Comparative Example 2 (Synthesis of Compound of Comparative Example)

The compound (2.9 parts) represented by the following formula (Y) was obtained as a red solid substance in the same manner as in Example 1 except that 4-t-butylbenzyl chloride (2.3 parts) in step (1-3) was replaced with 1-bromobutane (1.4 parts). The maximum absorption wavelength of the compound in methanol was 515 nm.

(Y)

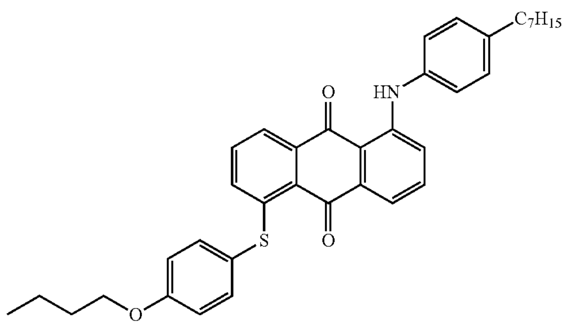

Reference Example (Transmittance Ratio of Anthraquinone Compounds of Examples and Comparative Examples at Maximum Absorption Wavelength)

Methanol solutions having the same concentration were individually prepared using the compound of Example 1 represented by No. 16 in the specific compound examples, the compound of Example 2 represented by No. 15 in the specific compound examples, the compound of Example 3 represented by No. 17 in the specific compound examples, the compound of Example 4 represented by No.26 in the specific compound examples, the compound of Example 5 represented by No.32 in the specific compound examples, the compound of Example 6 represented by No.34 in the specific compound examples, the compound of Comparative Example 1 represented by formula (X), the compound of Comparative Example 2 represented by formula (Y), and the compound represented by the following formula (Z) (i.e., a compound for reference with the maximum absorption wavelength in methanol being 520 nm). Then, the transmittance (%) of each of these compounds in the methanol solution at the maximum absorption wavelength was measured. The transmittance ratio of each of these compounds was obtained with the transmittance of the compound represented by No. 16 in the specific compound examples at the maximum absorption wavelength as a denominator. According to this calculation method, the transmittance ratio of the compound represented by No. 15 was 0.75; the transmittance ratio of the compound represented by No. 17 was 1.05; the transmittance ratio of the compound represented by No. 26 was 0.75; the transmittance ratio of the compound represented by No. 32 was 0.75, the transmittance ratio of the compound represented by No. 34 was 0.75; the transmittance ratio of the compound represented by the formula (X) was 0.95, the transmittance ratio of the compound represented by the formula (Y) was 0.85; and the transmittance ratio of the compound represented by the formula (Z) was 0.45.

(Z)

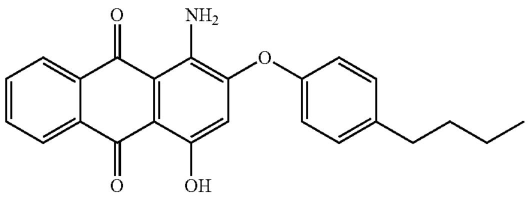

Example 7 (Preparation of Light Control Liquid Crystal Composition of Present Invention)

The compound of Example 1 (0.02 parts) represented by No. 16 in the specific compound examples, isobornyl acrylate (monoacrylate manufactured by Osaka Organic Chemical Industry) (0.380 parts), triethylene glycol dimethacrylate (manufactured by SHIN-NAKAMURA CHEMICAL CO., LTD.) (0.020 parts), 1-cyano-4'-n-pentylbiphenyl (0.306 parts), 1-cyano-4'-n-heptyl biphenyl (0.15 parts), 1-cyano-4'-n-octyloxybiphenyl (0.096 parts), 1-cyano-4"-n-pentylterphenyl (0.048 parts), Irgacure TPO (manufactured by BASF) (0.004 parts), Irgacure 184 (manufactured by BASF) (0.004 parts), and a spacer agent (Micropearl SP220 (registered trademark) manufactured by Sekisui Chemical Co., Ltd.) (0.010 parts) having a diameter of 20 μm were mixed at room temperature, stirred at 50° C. for two hours, cooled to room temperature, and passed through a 1 μm-membrane filter to prepare a liquid crystal composition of the present invention.

Example 8 (Preparation of Light Control Liquid Crystal Composition of Present Invention)

A liquid crystal composition of the present invention was prepared in the same manner as in Example 7 except that the compound of Example 1 (0.02 parts) represented by No. 16 in the specific compound examples was replaced with the compound of Example 2 (0.015 parts) represented by No. 15 in the specific compound examples (where the amount of 0.015 parts was determined by multiplication of the amount (0.02 parts) of the compound of Example 7 represented by No. 16 and the transmittance ratio (0.75) of the compound of Reference Example represented by No. 15).

Example 9 (Preparation of Light Control Liquid Crystal Composition of Present Invention)

A liquid crystal composition of the present invention was prepared in the same manner as in Example 7 except that the compound of Example 1 (0.02 parts) represented by No. 16 in the specific compound examples cited above was replaced with the compound of Example 3 (0.021 parts) represented by No. 17 in the specific compound examples (where the amount of 0.021 parts was determined by multiplication of the amount (0.02 parts) of the compound of Example 7 represented by No. 16 in the specific compound examples and the transmittance ratio (1.05) of the compound of Reference Example represented by No. 17 in the specific compound examples).

Example 10 (Preparation of Light Control Liquid Crystal Composition of Present Invention)

A liquid crystal composition of the present invention was prepared in the same manner as in Example 7 except that the compound of Example 1 (0.02 parts) represented by No. 16 in the specific compound examples was replaced with the compound of Example 4 (0.015 parts) represented by No. 26 in the specific compound examples (where the amount of 0.015 parts was determined by multiplication of the amount (0.02 parts) of the compound of Example 7 represented by No. 16 in the specific compound examples and the transmittance ratio (0.75) of the compound of Reference Example represented by No.26 in the specific compound examples).

Example 11 (Preparation of Light Control Liquid Crystal Composition of Present Invention)

A liquid crystal composition of the present invention was prepared in the same manner as in Example 7 except that the compound of Example 1 (0.02 parts) represented by No. 16 in the specific compound examples was replaced with the compound of Example 5 (0.015 parts) represented by No. 32 in the specific compound examples (where the amount of 0.015 parts was determined by multiplication of the amount (0.02 parts) of the compound of Example 7 represented by No. 16 in the specific compound examples and the transmittance ratio (0.75) of the compound of Reference Example represented by No. 32 in the specific compound examples).

Example 12 (Preparation of Light Control Liquid Crystal Composition of Present Invention)

A liquid crystal composition of the present invention was prepared in the same manner as in Example 7 except that the compound of Example 1 (0.02 parts) represented by No. 16 in the specific compound examples was replaced with the compound of Example 6 (0.015 parts) represented by No. 34 in the specific compound examples (where the amount of 0.015 parts was determined by multiplication of the amount (0.02 parts) of the compound of Example 7 represented by No. 16 in the specific compound examples and the transmittance ratio (0.75) of the compound of Reference Example represented by No. 34 in the specific compound examples).

Comparative Example 3 (Preparation of Light Control Liquid Crystal Composition for Comparison)

A liquid crystal composition for comparison was prepared in the same manner as in Example 7 except that the compound of Example 1 (0.02 parts) represented by No. 16 in the specific compound examples was replaced with the compound of Comparative Example 1 (0.019 parts) represented by formula (X) (where the amount of 0.019 parts was determined by multiplication of the amount (0.02 parts) of the compound of Example 7 represented by No. 16 in the specific compound examples and the transmittance ratio (0.95) of the compound of Reference Example represented by formula (X)).

Comparative Example 4 (Preparation of Light Control Liquid Crystal Composition for Comparison)

A liquid crystal composition for comparison was prepared in the same manner as in Example 7 except that the compound of Example 1 (0.02 parts) represented by No. 16 in the specific compound examples was replaced with the compound of Comparative Example 2 (0.017 parts) represented by formula (Y) (where the amount of 0.017 parts was determined by multiplication of the amount (0.02 parts) of the compound of Example 7 represented by No. 16 in the specific compound examples and the transmittance ratio (0.85) of the compound of Reference Example represented by formula (Y)).

Comparative Example 5 (Preparation of Light Control Liquid Crystal Composition for Comparison)

A liquid crystal composition for comparison was prepared in the same manner as in Example 7 except that the compound of Example 1 (0.02 parts) represented by No. 16 in the specific compound examples was replaced with the compound represented by formula (Z) (0.009 parts) (where the amount of 0.009 parts was determined by multiplication of the amount (0.02 parts) of the compound of Example 7 represented by No. 16 in the specific compound examples and the transmittance ratio (0.45) of the compound of Reference Example represented by formula (Z)).

Examples 13 to 18 and Comparative Examples 6 to 8 (Preparation of Light Control Elements of Present Invention and Comparative Examples)

Onto the ITO films of 5 cm-square PET films having ITO films formed thereon, the liquid crystal compositions obtained in Examples 7 to 12 and Comparative Examples 3 to 5 were applied by use of an applicator to form films with liquid crystal composition layers, respectively. Subsequently, each of these films and a 5 cm-square PET film having the same ITO film provided thereon were superimposed with each other such that the liquid crystal composition layer formed on the ITO film faces the other ITO film. Thereafter, while the thus formed laminate samples of two films and the liquid crystal composition layer were kept at 23° C. by a thermoplate, the samples were set at a position at which an LED lamp could apply light having a wavelength of 365 nm at a light intensity of 9 $mW/cm^2$, and the set samples were then irradiated with the light for one minute to cure the photocurable compounds to obtain light control elements of the present invention and for comparison.

Calculation of Transmittance Difference of Light control Element

The light control elements of Examples 13 to 18 and Comparative Examples 6 to 8 were subjected to measurement of transmittance (%) of light of maximum absorption wavelengths when an AC voltage of 100 V (50 Hz sine wave) was applied and not applied (light was blocked). From the measurement results, a transmittance difference (transmittance change) between the voltage application time and non-voltage application time in each of the examples was calculated. The results were shown in Table 1.

As shown in Table 1, these results reveal that the light control elements of Examples 13 to 18 were apparently excellent in contrast, because they exhibited larger transmittance differences between the voltage application time and non-voltage application time than light control elements of Comparative Examples 6 to 8.

TABLE 1

Measurement results of transmittance difference

| Light control element | Maximum absorption wavelength (nm) | Transmittance (voltage 0 V) (%) | Transmittance (voltage 100 V) (%) | Transmittance difference (%) |
|---|---|---|---|---|
| Example 13 | 518 | 15 | 61 | 46 |
| Example 14 | 513 | 16 | 60 | 44 |
| Example 15 | 515 | 15 | 58 | 43 |
| Example 16 | 515 | 16 | 61 | 45 |
| Example 17 | 513 | 16 | 60 | 44 |
| Example 18 | 513 | 16 | 59 | 43 |
| Comp. Example 6 | 518 | 15 | 53 | 38 |
| Comp. Example 7 | 515 | 15 | 54 | 39 |
| Comp. Example 8 | 520 | 15 | 42 | 27 |

Light Resistance Test of Light control Elements

The light control elements obtained in Examples 13 to 18 were each irradiated with light using a xenon lamp for 500 hours. Thereafter, the transmittances (%) at maximum absorption wavelengths were measured by the same method as that described in the above section "Calculation of Transmittance Difference of Light Control Element".

The light control elements obtained in Examples 13 to 18 exhibited no change in transmittance even after the light resistance test with a xenon lamp for 500 hours, indicating that the light resistance against long-time exposure to light was also excellent. From the results, it was demonstrated that the light control elements of Examples 13 to 18 were excellent in light resistance.

Example 19 (Preparation of Light Control Liquid Crystal Composition of Present Invention)

The compound of Example 1 (0.012 parts) represented by No. 16, 1-cyano-4'-n-pentylbiphenyl (0.306 parts), 1-cyano-4'-n-heptyl biphenyl (0.15 parts), 1-cyano-4'-n-octyloxybiphenyl (0.096 parts), and 1-cyano-4''-n-pentylterphenyl (0.048 parts) were mixed at room temperature to prepare a liquid crystal composition of the present invention.

Examples 20 to 24 and Comparative Examples 9 and 10 (Preparation of Light Control Liquid Crystal Composition of Present Invention and for Comparison)

The liquid crystal compositions of the present invention and for comparison were prepared in accordance with Example 19 except that the compound of Example 1 represented by No. 16 in the specific compound examples was replaced with the compound of Example 2 represented by No. 15 in the specific compound examples, the compound of Example 3 represented by No. 17 in the specific compound examples, the compound of Example 4 represented by No. 26 in the specific compound examples, the compound of Example 5represented by No. 32 in the specific compound examples, the compound of Example 6 represented by No. 34 in the specific compound examples, the compound of Comparative Example 1 represented by formula (X), and the compound of Comparative Example 2 represented by formula (Y), respectively.

Examples 25 to 30 and Comparative Examples 11 and 12 (Formation of Light Control Elements of Present Invention and for Comparison)

The liquid crystal compositions obtained in Examples 19 to 24 and Comparative Examples 9 and 10 were each encapsulated in an element made of two upper and lower glass substrates each having a transparent electrode with an inter-substrate gap of 15 μm, in which the surface of each glass substrate in contact with a liquid crystal was rubbed with a polyamide-based resin and was subjected to a homogeneous alignment treatment. In the element, when no voltage was applied, the liquid crystal was in a homogeneous alignment state and dye molecules were also in a similar alignment state according to the liquid crystal.

Calculation of Order Parameter (S value) of Light Control Element

To each of the light control elements obtained in Examples 25 to 30 and Comparative Examples 11 and 12, linear polarized light parallel to the alignment direction and linear polarized light vertical to the alignment direction were applied. Based on each of the spectra, the absorbance ($A_{//}$) of linear polarized light in parallel to the alignment direction of colored cells and absorbance ($A_{\perp}$) of linear polarized light in vertical to the alignment direction were measured. The order parameter (S value) at a maximum absorption wavelength (λmax) was obtained in accordance with the following formula. The results were shown in Table 2.

$$S=(A_{//}-A_{\perp})/(2A_{\perp}+A_{//})$$

TABLE 2

Calculation results of order parameter (S value)

| Light control element | Maximum absorption wavelength (nm) | S value |
|---|---|---|
| Example 25 | 523 | 0.74 |
| Example 26 | 522 | 0.72 |
| Example 27 | 522 | 0.72 |
| Example 28 | 523 | 0.73 |
| Example 29 | 522 | 0.72 |
| Example 30 | 522 | 0.72 |
| Comp. Example 11 | 523 | 0.68 |
| Comp. Example 12 | 523 | 0.69 |

As shown in the table, the light control elements of Examples 25 to 30 had higher order parameters than those of Comparative Examples 11 and 12, and thus, were apparently excellent as light control elements.

Light Resistance Test of Light Control Elements

The light control elements obtained in Examples 25 to 30 were each irradiated with a xenon lamp for 500 hours, and thereafter, transmittance (%) was measured at a maximum absorption wavelength in the same manner as in the above "Calculation of Order Parameter (S value) of Light Control Element".

The light control elements obtained in Examples 25 to 30 exhibited no variation in transmittance even after 500 hours in the xenon light-resistance test and thus had excellent light resistance against long-time exposure to light. From the results, it was demonstrated that the light control elements of Examples 25 to 30 were excellent in light resistance.

INDUSTRIAL APPLICABILITY

The anthraquinone compound of the present invention having a maximum absorption wavelength in a predetermined wavelength range and a high transmittance difference is excellent in light resistance. Use of a light control liquid crystal composition containing the anthraquinone compound can provide a light control element excellent in contrast. The light control element of the present invention can be used in outdoor building-material applications and vehicle applications requiring high durability.

The invention claimed is:

1. An anthraquinone compound represented by the following formula (1)

(1)

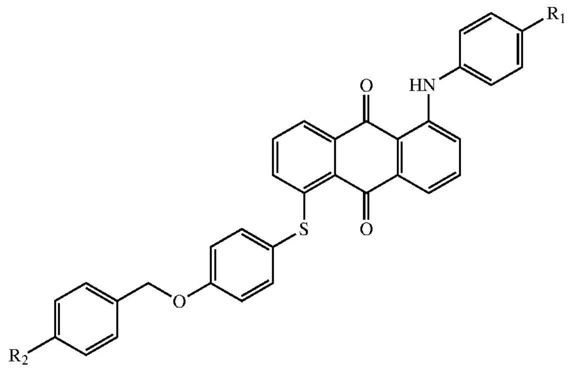

wherein $R_1$ represents a hydrogen atom, a linear or branched alkyl group having 1 to 12 carbon atoms, or a linear or branched alkoxy group having 1 to 12 carbon atoms, and $R_2$ represents a hydrogen atom, a linear or branched alkyl group having 1 to 8 carbon atoms, or a linear or branched alkoxy group having 1 to 8 carbon atoms.

2. The anthraquinone compound according to claim 1, wherein $R_2$ is a linear or branched alkyl group having 1 to 8 carbon atoms or a linear or branched alkoxy group having 1 to 4 carbon atoms.

3. The anthraquinone compound according to claim 2, wherein $R_2$ is a linear or branched alkyl group having 1 to 4 carbon atoms.

4. The anthraquinone compound according to claim 3, wherein $R_2$ is a branched alkyl group having 3 or 4 carbon atoms.

5. The anthraquinone compound according to claim 2, wherein $R_1$ is a linear or branched alkoxy group having 1 to 8 carbon atoms.

6. The anthraquinone compound according to claim 5, wherein $R_1$ is a linear or branched alkoxy group having 5 to 8 carbon atoms.

7. The anthraquinone compound according to claim 2, wherein $R_1$ is a linear or branched alkyl group having 4 to 10 carbon atoms.

8. The anthraquinone compound according to claim 7, wherein $R_1$ is a linear alkyl group having 5 to 8 carbon atoms.

9. The anthraquinone compound according to claim 2, having a maximum absorption wavelength within the range of 500 to 550 nm.

10. The anthraquinone compound according to claim 1, wherein $R_2$ is a linear or branched alkyl group having 1 to 4 carbon atoms and $R_1$ is linear or branched alkoxy group having 5 to 8 carbon atoms.

11. The anthraquinone compound according to claim 1, wherein $R_2$ is a linear or branched alkyl group having 1 to 4 carbon atoms and $R_1$ is a linear or branched alkyl group having 4 to 10 carbon atoms.

12. The anthraquinone compound according to claim 1, having a maximum absorption wavelength within the range of 500 to 550 nm.

13. A light control liquid crystal composition comprising the anthraquinone compound according to claim 1 and a liquid crystal material.

14. The light control liquid crystal composition according to claim 13, further comprising a dye compound other than the anthraquinone compound represented by formula (1).

15. The light control liquid crystal composition according to claim 13, further comprising a photocurable compound and a photopolymerization initiator.

16. A photocured product of the light control liquid crystal composition according to claim 15.

17. A light control element obtained by sandwiching the photocured product according to claim 16 between a pair of substrates disposed facing each other, at least one of which is a transparent substrate having a transparent electrode.

18. The light control element according to claim 17, wherein both of the pair of substrates are transparent substrates having a transparent electrode.

19. A light control element obtained by sandwiching the light control liquid crystal composition according to claim 13 between a pair of substrates disposed facing each other, at least one of which is a transparent substrate having a transparent electrode.

20. The light control element according to claim 19, wherein both of the pair of substrates are transparent substrates having a transparent electrode.

* * * * *